United States Patent
Fuerst et al.

(10) Patent No.: US 11,754,853 B2
(45) Date of Patent: Sep. 12, 2023

(54) SYSTEMS AND METHODS FOR THREE-DIMENSIONAL VISUALIZATION DURING ROBOTIC SURGERY

(71) Applicant: Verb Surgical Inc., Santa Clara, CA (US)

(72) Inventors: Bernhard A. Fuerst, Sunnyvale, CA (US); Pablo Garcia Kilroy, Menlo Park, CA (US); Joan Savall, Palo Alto, CA (US); Anette Lia Freiin Von Kapri, Mountain View, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 17/722,100

(22) Filed: Apr. 15, 2022

(65) Prior Publication Data

US 2022/0244566 A1  Aug. 4, 2022

Related U.S. Application Data (63) Continuation of application No. 17/112,855, filed on Dec. 4, 2020, now Pat. No. 11,333,899, which is a
(Continued)

(51) Int. Cl.
*A61B 34/35* (2016.01)
*G02B 30/26* (2020.01)
(Continued)

(52) U.S. Cl.
CPC .............. *G02B 30/26* (2020.01); *A61B 34/35* (2016.02); *G02B 27/0093* (2013.01); *G06F 3/013* (2013.01); *G06F 3/04817* (2013.01)

(58) Field of Classification Search
CPC ................ A61B 1/00048; A61B 34/35; G02B 27/0093; G02B 30/26; G06F 3/012;
(Continued)

(56) References Cited

U.S. PATENT DOCUMENTS 6,847,336 B1  1/2005  Lemelson et al.
8,784,206 B1  7/2014  Gronkowski et al.
(Continued)

FOREIGN PATENT DOCUMENTS

WO  2017210101  12/2017

OTHER PUBLICATIONS

International Preliminary Report on Patentability for International Applicaiton No. PCT/US2019/021475 dated Jan. 14, 2021, 12 pages.
(Continued)

*Primary Examiner* — Kathleen M Walsh
(74) *Attorney, Agent, or Firm* — AIKIN & GALLANT, LLP (57) ABSTRACT

An autostereoscopic three-dimensional display system for surgical robotics has an autostereoscopic three-dimensional display configured to receive and display video from a surgical robotics camera, and a first sensor assembly and a second sensor assembly. A processor is configured to detect and track an eye position or a head position of a user relative to the display based on processing output data of the first sensor assembly, and to detect and track a gaze of the user based on processing output data of the second sensor assembly. The processor further is configured to modify or control an operation of the display system based on the detected gaze of the user. A spatial relationship of the display also can be automatically adjusted in relation to the user based on the detected eye or head position of the user to optimize the user's visualization of three-dimensional images on the display.

16 Claims, 4 Drawing Sheets

Related U.S. Application Data continuation of application No. 16/287,964, filed on Feb. 27, 2019, now Pat. No. 10,895,757.

(60) Provisional application No. 62/693,850, filed on Jul. 3, 2018.

(51) Int. Cl.
*G02B 27/00* (2006.01)
*G06F 3/01* (2006.01)
*G06F 3/04817* (2022.01)

(58) Field of Classification Search
CPC ... G06F 3/013; G06F 3/04817; H04N 13/302; H04N 13/366; H04N 13/383
USPC .......................................................... 348/51
See application file for complete search history.

(56) References Cited

U.S. PATENT DOCUMENTS

| | | | |
|---|---|---|---|
| 8,878,895 B2 | 11/2014 | Yoon | |
| 10,895,757 B2 | 1/2021 | Fuerst et al. | |
| 11,333,899 B2* | 5/2022 | Fuerst | H04N 13/383 |
| 2002/0135738 A1 | 9/2002 | Cok et al. | |
| 2004/0156554 A1 | 8/2004 | McIntryre | |
| 2006/0238545 A1* | 10/2006 | Bakin | G09G 3/003 |
| | | | 345/613 |
| 2009/0248036 A1 | 10/2009 | Hoffman et al. | |
| 2009/0270678 A1 | 10/2009 | Scott et al. | |
| 2012/0275024 A1* | 11/2012 | Marzen | G02F 1/133528 |
| | | | 156/60 |
| 2013/0107207 A1 | 5/2013 | Zhao et al. | |
| 2013/0242053 A1 | 9/2013 | Bjelkhagen et al. | |
| 2013/0267317 A1 | 10/2013 | Aoki et al. | |
| 2014/0024889 A1* | 1/2014 | Xiaoli | A61B 34/30 |
| | | | 600/102 |
| 2014/0028546 A1 | 1/2014 | Jeon et al. | |
| 2014/0028548 A1 | 1/2014 | Bychkov et al. | |
| 2014/0153091 A1 | 6/2014 | Boudreau et al. | |
| 2015/0025547 A1* | 1/2015 | Hannaford | A61B 34/76 |
| | | | 606/130 |
| 2015/0049383 A1* | 2/2015 | Janins | G02B 30/10 |
| | | | 359/463 |
| 2015/0070481 A1 | 3/2015 | S. et al. | |
| 2015/0077313 A1 | 3/2015 | Gao et al. | |
| 2016/0104451 A1 | 4/2016 | Sahin | |
| 2016/0209647 A1 | 7/2016 | Fursich | |
| 2017/0099479 A1 | 4/2017 | Browd et al. | |
| 2017/0172675 A1 | 6/2017 | Jarc et al. | |
| 2017/0180720 A1 | 6/2017 | Jarc | |
| 2017/0235360 A1 | 8/2017 | George-Svahn | |
| 2018/0130209 A1 | 5/2018 | Price et al. | |
| 2019/0125184 A1 | 5/2019 | Kramer et al. | |
| 2019/0223968 A1 | 7/2019 | Jarc et al. | |
| 2019/0231456 A1 | 8/2019 | Ruiz Morales et al. | |
| 2019/0298481 A1* | 10/2019 | Rosenberg | G06F 3/013 |
| 2019/0327394 A1 | 10/2019 | Ramirez Luna et al. | |
| 2020/0015598 A1 | 1/2020 | Hondori et al. | |
| 2020/0015918 A1* | 1/2020 | Payyavula | B25J 9/1689 |
| 2020/0169724 A1* | 5/2020 | Meglan | A61B 34/35 |
| 2020/0363868 A1 | 11/2020 | Freiin von Kapri et al. | |
| 2021/0236233 A1 | 8/2021 | Fuerst et al. | |

OTHER PUBLICATIONS

Partial International Search Report and Written Opinion for International Application No. PCT/US2019/021475 dated Jun. 12, 2019, 16 pages.

International Search Report and Written Opinion for International Application No. PCT/US2019/021475 dated Aug. 7, 2019, 21 pages.

Unpublished U.S. Appl. No. 16/449,170, filed Jun. 21, 2019.
Unpublished U.S. Appl. No. 17/009,644, filed Aug. 31, 2020.
U.S. Appl. No. 62/967,810, filed Jan. 30, 2020.
Unpublished U.S. Appl. No. 16/815,748, filed Mar. 11, 2020.
Unpublished U.S. Appl. No. 17/020,722, filed Sep. 14, 2020.
U.S. Appl. No. 62/693,850, filed Jul. 3, 2018.

* cited by examiner

SYSTEMS AND METHODS FOR THREE-DIMENSIONAL VISUALIZATION DURING ROBOTIC SURGERY

CROSS-REFERENCE TO RELATED APPLICATION

The present application is a continuation of pending U.S. application Ser. No. 16/287,964 filed Feb. 27, 2019, which claims the benefit of United States Provisional Application Ser. No. 62/693,850 filed on Jul. 3, 2018.

INCORPORATION BY REFERENCE

U.S. Provisional Application No. 62/693,850, which was filed on Jul. 3, 2018, is specifically incorporated by reference herein as if set forth in its entirety.

TECHNICAL FIELD

This disclosure relates generally to the field of surgical robotics and, more particularly, to display systems for use with surgical robotic systems for visualizing the surgical site.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one endoscopic camera through the incisions into the patient. The surgical procedures are then performed by using the introduced tools, with the visualization aid provided by the camera.

Generally, MIS provides multiple benefits, such as reduced patient scarring, less patient pain, shorter patient recovery periods, and lower medical treatment costs associated with patient recovery. In some embodiments, MIS may be performed with surgical robotic systems that include one or more robotic arms for manipulating surgical instruments based on commands from an operator. For example, an operator may provide commands for manipulating surgical instruments, while viewing an image that is provided by a camera and displayed on a display to the user. However, conventional display systems fall short in enabling effective control of the display systems or of surgical robotic systems. Furthermore, conventional display systems generally provide two-dimensional (2-D) surgical image data to the user, and current three-dimensional (3-D) displays typically require the user to wear glasses or additional, similar wearable components (e.g., with polarizing filters or dynamic shutters) for visualization of three-dimensional images. Such glasses and additional wearable components, however, may be problematic to use and handle in surgical or sterile environments. Thus, there is a need for improved 3-D display systems that enable a user to better visualize the surgical site during robotic surgery.

SUMMARY

Generally, a three-dimensional display system for use with a surgical robotic system can include a three-dimensional display configured to receive and display video from a surgical robotics camera, such as an endoscopic camera. The display system can include a plurality of sensor assemblies having a first sensor assembly and a second sensor assembly. The first sensor assembly and the second sensor assembly can be coupled to or integrally formed with the display. The display system can include a processor or controller configured to detect and track an eye position or a head position of a user relative to the display based on processing output data of the first sensor assembly. The processor or controller also can be configured to detect and track a gaze of the user based on processing output data of the second sensor assembly.

The processor or controller further is configured to modify or control an operation of the display system based on the detected and tracked gaze of the user, for example, to facilitate control of the display system with the user's eyes or eye motions. In addition, a spatial relationship of the display can be automatically adjusted in relation to the user based on the detected eye or head position of the user. For example, a distance or orientation between the detected eye or head position and the display can be automatically (e.g., without requiring deliberate user input) updated to adjust the user's visualization of three-dimensional image data from the surgical robotics camera on the display.

In some variations, the display can include a panel display or monitor, such as an LCD, LED, plasma, or other suitable flat, curved, or otherwise shaped panel display or monitor, having a plurality of pixels for displaying two or three-dimensional images. The display further can include one or more layers at least partially positioned over the panel display and configured to facilitate a user's visualization of three-dimensional images on the panel display. The one or more layers can include a polarizing filter, a pattern retarder, or dynamic shutters that allow users to uses glasses or other wearable components to view or visualize the three-dimensional images on the panel display. Alternatively, the one or more layers can include layers of micro-lenses that can at least partially cover the plurality of pixels of the panel display. The layer(s) of micro-lenses further can be positioned or disposed in relation to the plurality of pixels to facilitate or otherwise allow the user's visualization or perception of three-dimensional images on the panel display, without the use of three-dimensional glasses or other additional wearable or similar components worn by a user. The display further can include a protective layer at least partially disposed over or sealing off the layer(s) of the panel display. The protective layer can be bonded to layer(s) or the panel display using an adhesive, such as an optically clear adhesive or other suitable adhesive. An additional protective layer can be provided on the display panel, e.g., between the one or more layers including micro-lenses and the display panel.

In some variations, the first sensor assembly can include at least one camera, such as a stereo camera, an infrared camera, or other suitable camera that does not filter infrared light, e.g., to allow for detection and tracking of a head or eye position of a user (e.g., an xyz position of the user's head or eye position in relation to an origin or original position or to the display). The second sensor assembly can include one or more cameras and a plurality of strobes or strobe lights, e.g., to allow for illumination of and detection and tracking of an iris or irises of the user's eyes.

In addition, a seat assembly can be provided with the display system. The seat assembly can have a seat in which a user is to sit or otherwise engage, while the user is viewing the display. The seat assembly also can include a movable or adjustable seat support assembly that is connected to and at least partially supports the seat. The processor or controller can automatically generate and send one or more signals or other output data to an actuator subsystem of the seat support assembly to adjust or update a position or orientation of the seat based upon received output data from the first or second sensor assemblies. For example, the position or orientation of the seat can be adjusted based on the detected and tracked eye or head position of the user to optimize the user's visualization of three-dimensional images on the display.

The display system also can include a movable or adjustable display support assembly connected to and supporting the display. The processor or controller can automatically generate and send one or more signals or other output data to an actuator subsystem of the movable or adjustable display support assembly to adjust or update a position or an orientation of the display based upon received output data from the first or second sensor assemblies. For example, the position or orientation of the display can be adjusted based on the detected and tracked eye or head position of the user to optimize the user's visualization of three-dimensional images from the surgical robotics camera on the display.

In one example, the position or orientation of the seat or the display can be automatically adjusted or changed such that the user's head or eyes are located at a predetermined distance from or orientation in relation to the display.

In some variations, the processor or controller can be in communication with the surgical robotic system. The processor further can be operable to send a signal or other output data to the surgical robotic system, e.g., to a controller thereof, for control of the surgical robotic system based on received output data from the first or second sensor assemblies. For example, when the gaze of the user is not directed towards the display, e.g., for a predetermined time interval, control of one or more operations of the surgical robotic system (e.g., operations of robotic arms or surgical instruments) may be paused or otherwise disabled.

Additionally, an endoscopic image or other suitable image of a surgical site from the surgical robotics camera may be displayed on the display, e.g., as part of a GUI or display window on the display. Control panels or side panels having a plurality of icons or images additionally or alternatively can be displayed on the display. For example, control or side panels can be positioned to the left and right of the primary display or window on the display. The plurality of icons or images can be related to applications for the display system or the surgical robotic system. The detected and tracked gaze of the user further can be used to initiate or control the applications in the control/side panels. For example, a user can focus their gaze on the images or icons shown the control or side panels to trigger application interactions (e.g., to start and stop a timer application, initiate or control an x-ray viewing tool, enlarge a view, or to initiate or control other suitable applications).

In some variations, a position or orientation of the surgical robotics camera can be dynamically or continuously updated based on the detected and tracked gaze of the user. For example, the position of the surgical robotics camera can be automatically updated such that an area or point substantially focused on by the user's gaze, e.g., an area or point within the primary display or window showing the endoscopic image, is substantially centered on the display. In one embodiment, when the processor or controller determines that the detected gaze of the user is directed at an area or point that is spaced apart from the center of the display, the processor or controller generates and sends a signal to the surgical robotics camera to adjust the position or orientation of the surgical robotics camera such that the area or point at which the user's gaze is directed or focused on is moved to the center of the display.

Furthermore, a method for three-dimensional visualization during robotic surgery can be provided. The method can be performed by a digital programmed processor executing instructions stored in a computer readable memory. The method can include receiving and displaying video from a surgical robotics camera on a three-dimensional display. The method further can include detecting and tracking a head position or an eye position of a user relative to the display based on processing output data of a first sensor assembly, and detecting and tracking a gaze of the user based on processing output data of a second sensor assembly. The detected and tracked gaze of the user can be used to facilitate control or modify operations of a display system or a surgical robotic system. In addition, the method can include automatically (e.g., without requiring deliberate user input) signaling an actuator subsystem to adjust or update a spatial relationship of the display in relation to the user based on the detected eye or head position of the user to optimize the user's visualization of three-dimensional images from the surgical robotics camera on the display.

In some variations, a position or orientation of the display or a seat assembly, which is configured to be sat in or otherwise engaged by the user when viewing the display, can be automatically adjusted or modified based upon the detected and tracked head or eye position of the user.

In further variations, an operation(s) of the surgical robotic system or display system also can be modified or otherwise controlled based on the detected and tracked gaze of the user. For example, the processor or controller can automatically signal an actuator subsystem of the surgical robotics camera to update or alter a position of a lens of the surgical robotics camera based on the gaze of the user. More specifically, the position or orientation of the surgical camera can be automatically altered or updated such that the point or area focused on by the user's gaze is substantially centered on/along the display. Further, when the detected and tracked gaze of the user is directed at an image or icon that is related to an application, e.g., an image or icon of a control or side panel displayed on the display, the application can be initiated or otherwise controlled. Still further, when the detected and tracked gaze of the user is not directed at the display, e.g., for a predetermined time interval, an operation of the surgical robotic system can be disabled.

DETAILED DESCRIPTION

Non-limiting examples of various aspects and variations of the invention are described herein and illustrated in the accompanying drawings.

Figure 1:
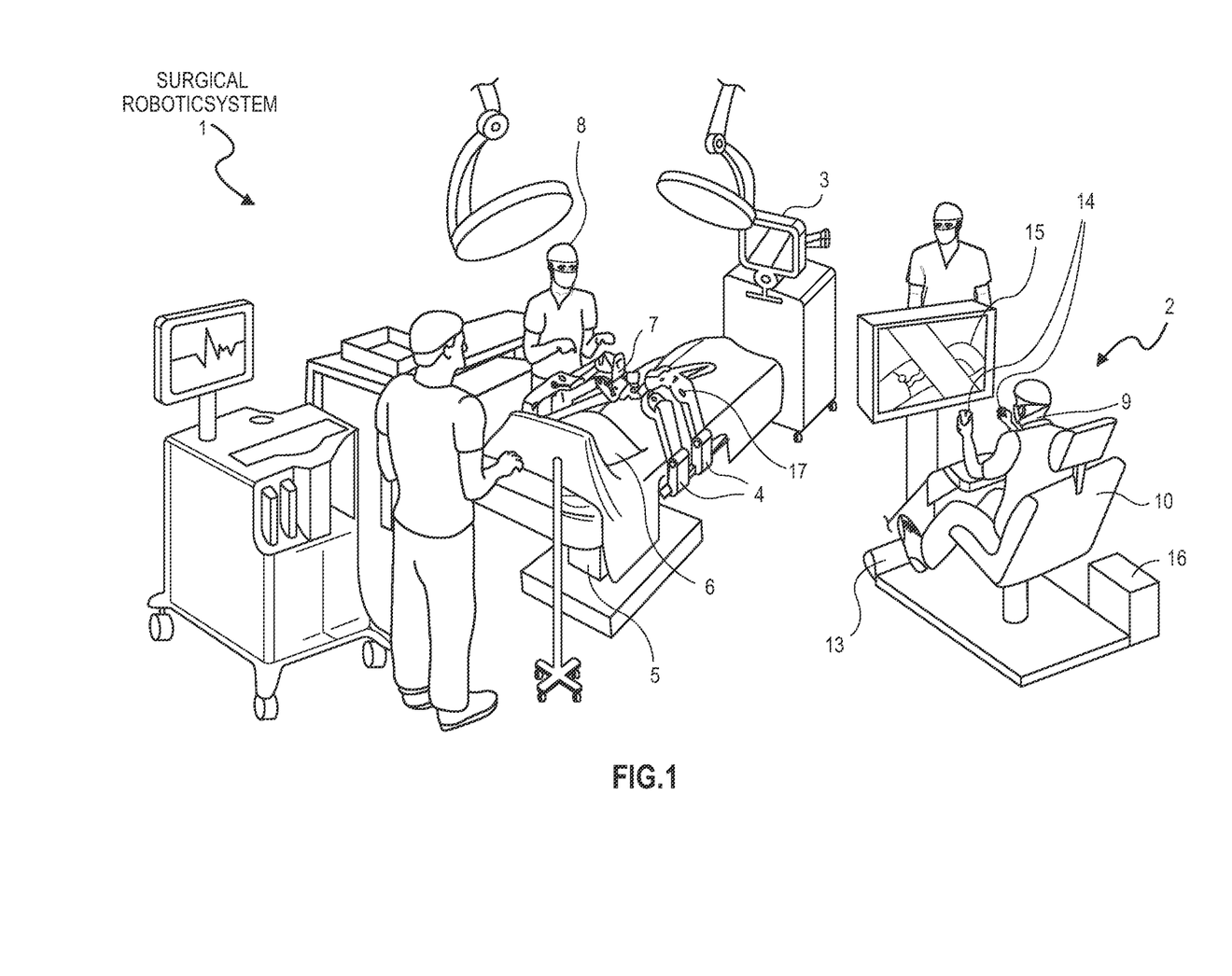
FIG. 1 is a pictorial view of an example surgical robotic system in an operating arena.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In one embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 or the attached surgical tools 7, e.g., teleoperation. The user console 2 may be located in the same operating room as the rest of the system 1, as shown in FIG. 1. In other environments, however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilising the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired or wireless links, using any suitable ones of a variety of data communication protocols. Any wired connections may be optionally built into the floor or walls or ceiling of the operating room. The robotic system 1 may provide video output to one or more displays, including displays within the operating room as well as remote displays that are accessible via the Internet or other networks (e.g., the robotic system 1 can include one or more endoscopic cameras that provide video output or other suitable image data to the displays). The video output or feed may also be encrypted to ensure privacy and all or portions of the video output may be saved to a server or electronic healthcare record system.

Figure 2:
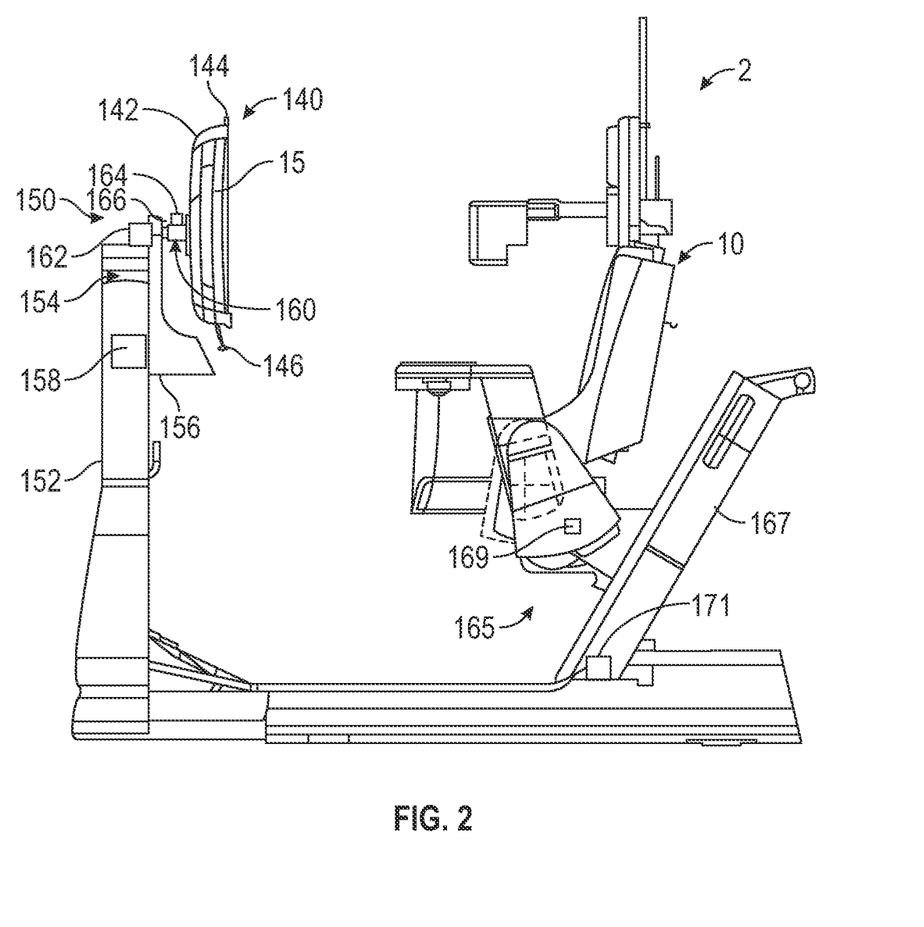
FIG. 2 shows a schematic view of an exemplary console for use with the surgical robotics system.

FIG. 2 shows a schematic view of an exemplary user console 2. As shown in FIG. 2, a display system 140 can be provided for use with the user console 2 and the surgical robotic system 1. The display system 140 includes an autostereoscopic, three-dimensional monitor or display 142 configured display three-dimensional (3D) or two-dimensional (2D) information to a user. The monitor 142 may display various information associated with the surgical procedure (e.g., an endoscopic camera view of the surgical site, static images, GUIs, etc.) or surgical robotic system (e.g., status, system settings), or other suitable information in the form of 2D and 3D video, image data, text, graphical interfaces, warnings, controls, indicator lights, etc. The monitor 142 as described herein further may enable the user to interact with displayed content using eye movements or other suitable gestures of the user for control of the display system and operation of other instruments such as those in the surgical robotic system.

FIG. 2 additionally shows that the display system 140 includes a plurality of sensor assemblies 144 and 146 including a first or head (or eye) tracking sensor assembly 144, and a second or gaze tracking sensor assembly 146. The first and second sensor assemblies 144 and 146 can be attached to, or in some variations integrally formed with, the monitor 142. For example, the first sensor assembly 144 can be connected to an upper or top portion of the monitor 142 and the second sensor assembly 146 can be connected to a lower or bottom portion of the monitor 142, as generally shown in FIG. 2. However, in the alternative, the second sensor assembly 146 can be attached to the top portion of the monitor 142 and the first sensor assembly 144 can be attached to the bottom portion of the monitor 142, or both the first and second sensor assemblies 144 and 146 can be attached to the top or bottom portions of the monitor 142, or the first or second sensor assemblies 144 and 146 can be attached to side portions of the monitor 142. The first or second sensor assemblies 144 and 146 also can be coupled to or incorporated with other suitable components or parts of or near the console 2, without departing from the scope of the present disclosure.

As further shown in FIG. 2, the monitor 142 may be supported by a power adjustable monitor support assembly 150. The monitor 142 may be positioned proximate or near the seat 10 to enable a user to view the monitor while the user is seated in or otherwise engaged by the seat 10. For example, the support assembly 150 may have a support or column 152 positioned in front or forward of the seat 10, which support or column 152 at least partially supports the monitor 142. In one variation, the monitor 142 is connected to the support 152 by an adjustable mount assembly 154 including an actuator subsystem with one or more actuators 158, 162, 166 that enable automatic adjustment of a position or orientation of the monitor 152 (e.g., based upon output data received from the first or second sensor assemblies 144 or 146). The monitor 142 further can include one or more sensors (e.g., position sensors, motion sensors, accelerometers, etc.) attached to the monitor 142 that facilitate the detection and tracking of positions or orientations of the monitor.

The mount assembly 154 can enable translation or rotational movement of the monitor 142 for up to six degrees of freedom including, e.g., tilt, yaw, rotation, front-to-back movement, side-to-side movement, and up-and-down movement. For example, the mount assembly 154 can include a slidable support portion or member 156 coupled to the monitor 142. The slidable support portion 156 further can be driven by one or more actuators 158 (e.g., motors, hydraulic actuators, pneumatic actuators, etc.) for up-down and side-to-side translation of the monitor 142. The mounting assembly 154 further can include one or more telescoping portions or sections 160 or other suitable portions or components that are driven by one or more actuators 162 to enable forward and backward movement of the monitor 142 (i.e., movement of the monitor 142 towards and away from the seat 10, e.g., to vary a distance between the seat 10 and the monitor 142). The telescoping portions 160 can connect the monitor 142 to the slidable support portion 156. The mounting assembly 154 also can include a pivotable connection 164 (e.g., a swivel fixture, ball joint, pivoting feature, etc.) connecting the monitor 142 to the telescoping portions 160. Movement of the monitor 142 about the pivotable connection 164 can be driven by an actuator 166 (e.g., motors, hydraulic actuators, pneumatic actuators, etc.) to enable tilt, yaw, and rotation of the monitor 142. The mounting assembly 154 further can allow for manual adjustment of the position or orientation of the monitor 142.

FIG. 2 further shows that the seat 10 can be supported by a power adjustable seat support assembly 165. The power adjustable seat support assembly 165 can have an actuator subsystem including actuators 169/171 that drive movement of the seat 10. As shown in FIG. 2, the seat support assembly 165 includes seat support 167 having a single pillar at least partially supporting the seat 10, but in other examples, the seat support 167 may comprise two or more pillars. The seat support 167 can be angled posteriorly in relation to the monitor 142, but in other variations, may be angled vertically straight upward or tilted anteriorly. In some variations, the seat 10 can be moveably or adjustably mounted to the seat support 167. For example, the seat 10 can rotate, tilt, recline, etc. in relation to the support 167 to enable adjustment of a position or orientation of the seat 10 in relation to the monitor 142 (e.g., such that a position of the user's head or eyes can be automatically adjusted in relation to the monitor 142 to optimize visualization or perception of three-dimensional images thereon). The seat assembly 165 further can have one or more actuators 169 (e.g., motors, hydraulic actuators, pneumatic actuators, etc.) for automatically driving rotation, tilting, reclining, etc. of the seat 10 (e.g., in response to output data from the first or second sensor assemblies 144/146).

In some variations, the seat 10 further is moveable along the support 167 (e.g., to move the seat 10 up and down and forward and backward in relation to the monitor 142). For example, an actuator 171 (e.g., a motor, a hydraulic actuator, a pneumatic actuator, etc.) can drive movement of the seat 10 along the support 167 (e.g., in response to output data from the first or second sensor assemblies 144/146). In addition, or in the alternative, the seat support 167 may be configured to change its angle or orientation, or to translate in the forward or rearward directions or in the lateral directions. In some further variations, the seat support 167 may be configured to telescope or otherwise extend or retract longitudinally or generally vertically. The seat support assembly 165 further may allow for manual adjustment the position or orientation of the seat 10.

Figure 3:
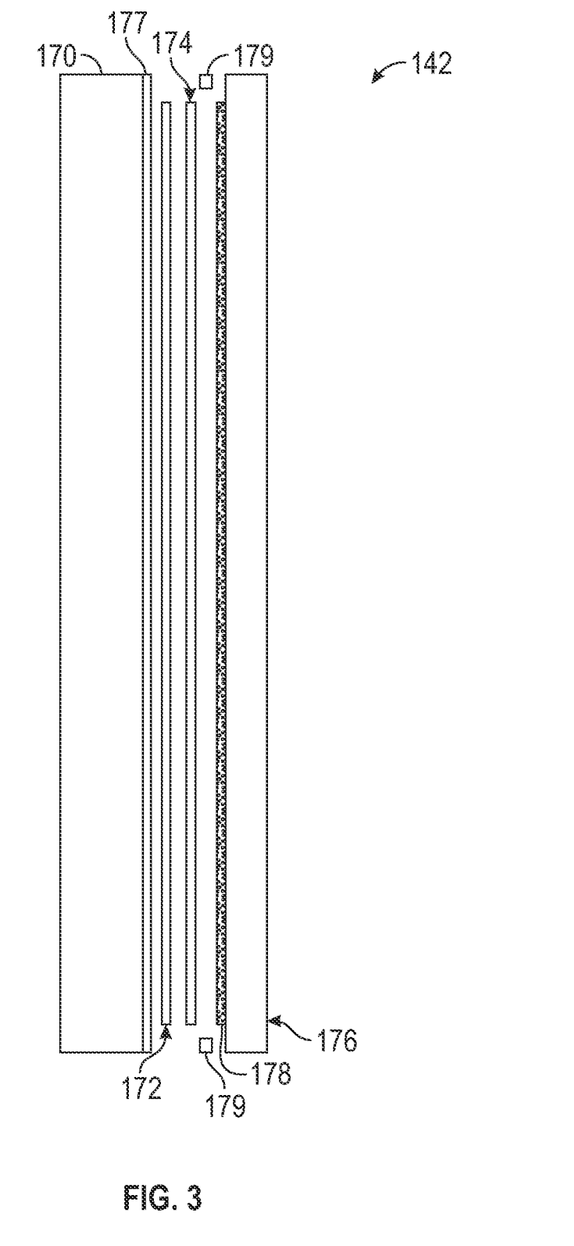
FIG. 3 shows an exploded side view of an exemplary display or monitor.

FIG. 3 shows a cross-sectional view of the display or monitor 142. The display or monitor 142 can include a flat, curved, or otherwise shaped panel display 170, such as an LCD, LED, plasma, or other suitable panel display, having a plurality of pixels for displaying two or three-dimensional images. The display 142 further can include one or more layers 172/174 at least partially overlaying, or otherwise disposed/positioned over, the display 142. The layers 172/174 are configured to facilitate a user's visualization of three-dimensional images on the display 142. In one embodiment, the layers 172/174 can include micro-lenses that can be at least partially positioned over the plurality of pixels of the panel display 170 to facilitate or otherwise allow for the user's visualization or perception of three-dimensional images on the panel display 170. In one embodiment, the pixels of the panel display 170 can display a left eye image and a right eye image that are continuously and/or dynamically interleaved, and the layers 172 or 174 can enable the user to visualize or perceive the left eye image and the right eye image as a single three-dimensional image, without the use of three-dimensional glasses or other additional wearable or similar components on the user. In the alternative, the one or more layers 172/174 can include polarizing filters, a patterned retarder, or dynamic shutters, and a user may use three-dimensional glasses or other similar wearable components to view or visualize three-dimensional images on the display.

The display 142 further can include a protective layer 176 at least partially covering or sealing off the layer(s) 172/174 or the panel display 170. The protective layer 176 may seal off and protect the layers 172/174 and panel display 170 such that the monitor 142 is suitable for use in a surgical environment. For example, the protective layer 176 may allow for sterilization or cleaning of the display (e.g., with cleaning chemicals, such as alcohol-based or chlorine-based cleaners) without damage to the micro-lenses 172/174. In one embodiment, the protective layer 176 can include surgical-grade glass or other surgical-grade materials (e.g., surgical-grade plastics or other suitable composite materials). The protective layer 176 further can have a thickness in the range of approximately 1 mm to approximately 3.0 mm, such as approximately 2.0 mm or other suitable integer and non-integer numbers therebetween. Thicknesses of less than 1.5 mm or greater than 3.0 mm can be employed, however, without departing from the scope of the present disclosure. Additionally, or in the alternative, at least one additional protective layer 177 can be provided on the panel display 170 (e.g., between the panel display 170 and the layer(s) 170). The additional protective layer 177 can have a thickness of up to 1.0 mm, such as approximately 0.3 mm, and can be formed from plastic, glass, or other suitable material.

The protective layer 176 can be bonded to one or both of the layers 172/174 or the panel display 170 using an adhesive 178 (e.g., an optically clear adhesive or other suitable adhesive or glue). One or more spacers 179 further may be provided between the protective layer 176 and the layers 172/174 or the panel display 170. The spacers 179 can be positioned along a boundary of the protective layer 176 at equally spaced intervals, though in some variations the spacers 179 can be disposed intermittently or sporadically about the protective layer 176. The spacers 179 can prevent damage to the layers 174/176 during formation of the monitor, e.g., during application and bonding of the protective layer 176.

Figure 4:
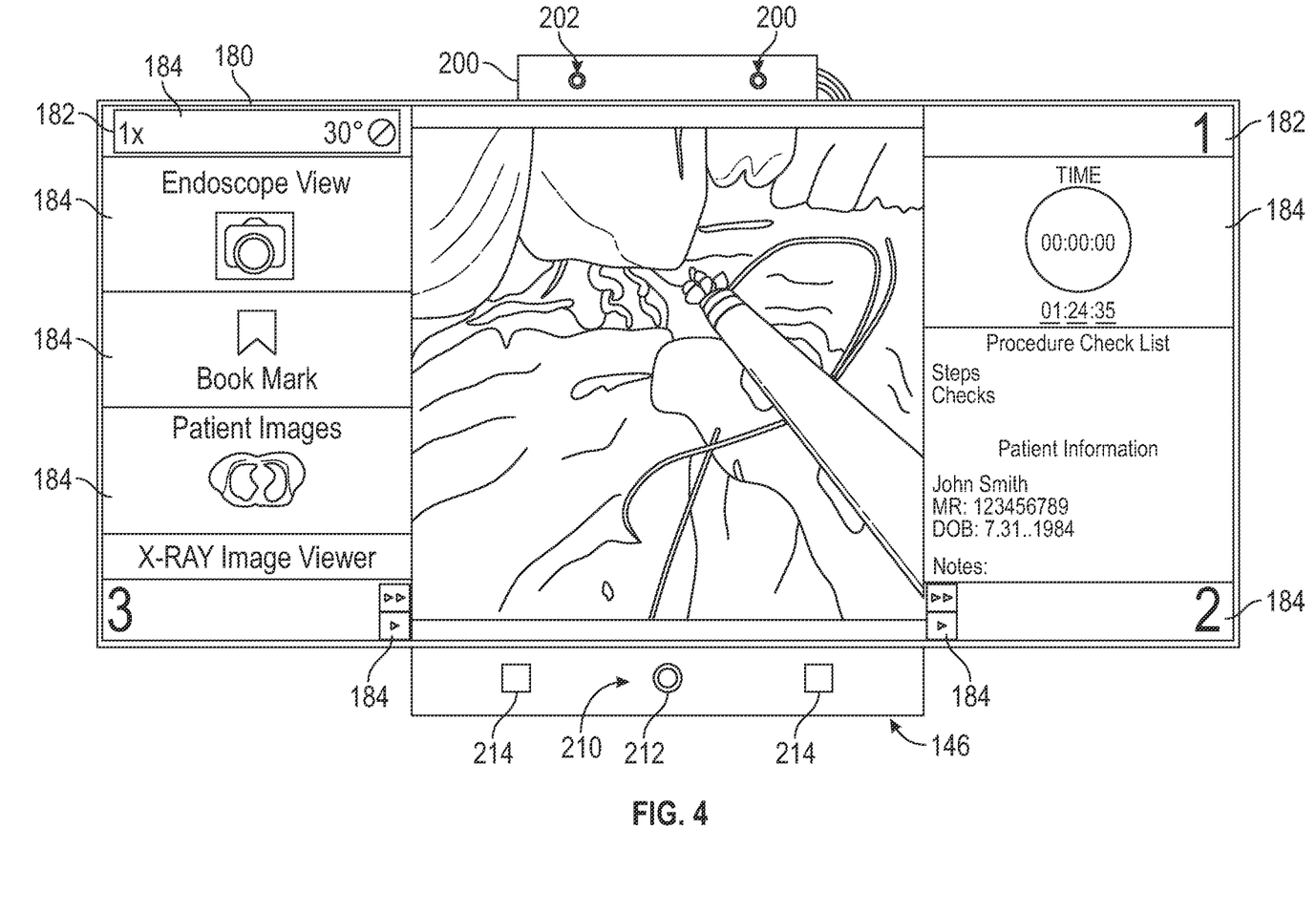
FIG. 4 shows an exemplary display system for use with the surgical robotics system.

As shown in FIG. 4, in some variations, the first sensor assembly 144 can include one or more sensors 200. The sensors 200 can include a stereo camera(s), an infrared camera(s), or other suitable camera(s) 202 that does not filter infrared light. In one embodiment, the camera(s) 202 can include one Intel® Real Sense Camera as provided by Intel Corp. of Santa Clara, Calif. The sensors 200 additionally or alternatively can include other types of cameras, e.g., color cameras, or other suitable sensing devices, without departing from the scope of the present disclosure. Signals or output information from the first sensor assembly 144 can be received and processed, e.g., by a controller or processor in communication with the first sensor assembly 144, to facilitate or otherwise allow for detection and tracking of a head or eye position of a user. For example, the first sensor assembly 144 can be used for detecting and tracking an xyz position of a user's head, eye, or eyes, e.g., in relation to an origin or an original position, such that a position, e.g., a distance, of the user's head or eyes can be continuously determined in relation to the monitor 142.

In addition, in some variations, the second sensor assembly 146 includes one or more sensors 210, such as one or more cameras 212, and one or more strobes or strobe lights 214, e.g., that flash light to facilitate detection and tracking of a gaze of a user by the camera(s) 212. The gaze of the user is detected based on a position or a movement of at least one iris of the user's eyes and includes an area or point at which the user is looking or substantially focused (e.g., an area or point on the monitor or an area or point off/away from the monitor). In one embodiment, the strobe(s) 214 can be configured to provide multiple flashes of light per second, e.g., flashes of light at a frequency in the range of approximately 80 Hz to approximately 100 Hz, such as approximately 90 Hz or other suitable frequency. The camera 212 includes a high-speed camera that is configured to capture the illuminated (e.g., by the strobes 214) and unilluminated irises of the user (e.g., such that the processor receiving and processing output data from the camera 212 can detect and track a user's irises to determine a point or area at which the user is looking or substantially focused on). The light flashes from the strobes 214 further may assist in perception of the user's eye or head position with the first sensor assembly 144, e.g., during low light conditions.

It should be understood that although some specific examples of sensor types, sensor locations, and sensor functions in the display system have been discussed above, a wide variety of other sensors and sensor types may additionally or alternatively be located throughout the various components of the display system in order to capture information about the user or for receiving user input as interactive user controls.

An example of a graphical user interface (GUI) to be displayed on the monitor 142 is shown in FIG. 4. For example, the GUI may display a display portion or display window 180 showing endoscopic image or other suitable surgical image data (e.g., from an endoscopic camera or other suitable surgical robotics camera placed inside the patient). The GUI may further include control panels or side panels 182 including one or more images or icons 184 related to one or more applications related to the surgical robotic system 1 (e.g., a timer application, an x-ray imaging tool, etc.). The control panel(s) 182 also can include other suitable information, such as one or more medical images (e.g., pre-operative images of patient tissue), patient data (e.g., name, medical record number, date of birth, various suitable notes, etc.), tool information (e.g., a left or right tool number, a left or right tool name, a left or right tool function, etc.). Other suitable GUIs or other display content may appear on the monitor without departing from the present disclosure. Various user interactions (e.g., the user's gaze or eye or head movements) also may cause changes to the displayed content type, as well as interaction with the applications as further described below.

The display system 140 generally includes or is in communication with a processor or controller configured to detect and track a head position or an eye position of a user relative to the monitor 142 based on processing output data of the first sensor assembly 144. In some variations, a spatial relationship between the monitor 142 and a user (e.g., a user sitting in seat 10) can be adjusted based on the detected eye or head position of the user, e.g., to optimize the user's visualization or perception of three-dimensional image data from the endoscopic or surgical robotics camera on the monitor 142. A user's perception of three-dimensional images on the monitor 142 may be optimal when the user's eyes are substantially centered with respect to the monitor 142 and spaced at a prescribed distance therefrom (e.g., approximately 70 cm to approximately 90 cm, such as approximately 80 cm from the monitor). Thus, the position or orientation of the seat 10 or the monitor 142 can be automatically (e.g., without requiring a deliberate user input) adjusted or changed to ensure that the user's head or eyes are located and positioned at an optimal orientation or viewing distance in relation to the monitor.

In one embodiment, the processor or controller can be in communication with the seat actuators 169 and 171 or the monitor actuators 158, 162, 166 and can automatically provide signals or information to seat actuators 169/171 or monitor 158, 162, 166 to adjust a position or orientation of the seat 10 or monitor 142 based upon processing output signals from the first or second sensor assemblies 144/166. For example, the processor or controller can determine a position of the user's head (or eyes) in relation to the monitor 142, and the processor can automatically generate and send a signal(s) to the seat actuators 169 or 171 or the monitor actuators 158, 162, or 166 to adjust or change the position or orientation of the seat or monitor (e.g., the seat can be reclined, tilted, rotated, moved up or down, moved side to side, etc. or the monitor can be tilted, yawed, rotated, moved front-to-back, moved side-to-side movement, moved up-and-down, etc.) based on the determined position of the user's head (or eyes), e.g., to optimize the user's visualization of three-dimensional images from the surgical robotics camera on the monitor. For example, the position or orientation of the seat or monitor can be adjusted such that the user's head (or eyes) is substantially centered with respect to the monitor and is at a prescribed distance from the monitor for optimal viewing of three-dimensional images.

The processor or controller additionally, or alternatively, can generate and send signals to the monitor 142 to display instructions thereon for manual adjustment of the monitor 142 or the seat 10 to optimize the user's perception or visualization of three dimensional image data on the display.

Furthermore, the controller or processor is configured to detect the track the gaze of the user based on processing output data of the second sensor assembly 146, and in some variations, operations of the display system 140 or the surgical robotic system 1 can be modified or controlled based on the detected gaze of the user (e.g., to facilitate control of the display system with the user's eyes or eye gestures or to stop or pause operations of the display system or surgical robotic system when the detected gaze of the user is directed away from the monitor).

In some variations, the processor or controller can be in communication with the surgical robotic system 1, and when the processor or controller determines that the gaze of a user is not directed at the monitor 142 (e.g., for a predetermined time period, such as approximately 3 seconds or up to approximately 5 seconds or more), the processor or controller is operable to automatically send a signal(s) or other output data to the surgical robotic system 1 or the display system 140 to activate or disable one or more operations thereof (e.g., to disable or freeze operation of one or more subsystems of the surgical system, such as the robotic arms 4 or the surgical tools 7, or to generate an alarm with the display system).

In one embodiment, when the processor or controller determined that the user's gaze is not directed at the monitor 142, e.g., for a prescribed time period, such as when the user is distracted, falls asleep, etc., the processor or controller automatically generates and sends one or more signals to the surgical system 1 to freeze or pause operation of the robotic arms 4 or the surgical tools 7, e.g., to prevent injury to a patient being operated on. Further, when the processor or controller determines that the user's gaze has returned to the monitor 142, the processor or controller may automatically generate and send one or more signals to the surgical system to resume operation of the robotic arms 4 or the surgical tools 7. However, the processor or controller may require a specific user input (e.g., selection of an icon, a gesture, etc.) prior to sending the signal(s) for resuming operation of the robotic arms or surgical tools 7.

Additionally, or in the alternative, when the processor or controller determines that the user's gaze is not directed at the monitor 142, the processor or controller may generate and send a signal(s) to the display system 140 to activate one or more alarms or notifications to get the attention of the user or other suitable entity (e.g., a speaker of the display system may play one or more audio sounds, the monitor may display one or more images indicating that the user's gaze is not directed at the monitor, or one or more vibrations or haptics of the seat or UIDs may be activated).

In some variations, the detected and tracked gaze of the user also can be used to initiate or control the applications on the control/side panels 182. For example, a user can look at or focus on the one or more images 184 on the control or side panels 182 to trigger application interactions. The user can initiate or close the applications, open the applications in one or more new windows or pop-up windows, control features or operations of the applications, etc. by focusing on or looking at one or more areas or points on the GUI or using other suitable eye motions. In one example, the user can focus on or look at an image associated with a timer application shown on the control/side panels, e.g., to start and stop the timer. In another example, the user can focus on or look at an image associated with an x-ray imaging tool to initiate the x-ray imaging tool (e.g., to open the x-ray imaging tool on one or more secondary or popup windows on the display). The user's gaze further can be used to close the x-ray image tool (e.g., when the user looks away or focuses on a close icon or image or other suitable feature).

Additionally, a position or orientation of the surgical robotics camera also can be updated or adjusted based on the detected and tracked gaze of the user. In some variations, the position or orientation of the surgical robotics camera can be continuously or dynamically updated (e.g., the controller or processor can automatically generate and send signals to an actuator subsystem of the surgical robotics camera to tilt, rotate, or otherwise translate a lens of the surgical robotics camera) such that an area or point on the monitor 142 that is being focused on by the user is substantially centered along the monitor 142 (e.g., centered in relation to the horizontal axis and the vertical axis of the monitor) where perception or visualization of three-dimensional image data is optimal. That is, each time a user focuses on an area or point of the three-dimensional image data displayed in the display window 180 that is not substantially centered along the display window 180 (e.g., based on the user's detected gaze), the position or orientation of the surgical robotics camera can be updated or changed such that the area or point of the three-dimensional image data on which the user is focused is moved or otherwise adjusted along the display window 180 so as to be substantially centered therealong.

For example, the user may initially focus on a point or area of the three-dimensional image data that is substantially centered within the display window 180, and when the user changes their focus or otherwise redirects their gaze to a new area or point on the image data shown in the display window 180 (e.g., the user looks at or focuses on an area or point that is proximate to or near an edge or corner of the display window 180 or the user looks at or focuses on an area or point that is otherwise spaced apart from the original point or area in the center of the display window), the processor or controller may generate and send one or more signals to the surgical robotics camera (or a controller thereof) to automatically adjust the position or orientation of the surgical robotics camera such that the new area or point of the three-dimensional image data that is focused on by the user is moved or adjusted so as to be substantially centered within the display window 180. In this way, the position or orientation of the surgical robotics camera can be continuously or dynamically adjusted or otherwise updated based upon the determined gaze of the user such that the user's focus is directed to be and remains generally centered along the display window to facilitate optimal three-dimensional perception or visualization of the three-dimensional image data displayed therein.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A display system, comprising:
an autostereoscopic three-dimensional (3D) display comprising a panel display and a-two micro-lenses layers positioned over the panel display to display a left eye image and a right eye image for visualization of three-dimensional images on the 3D display without use of eyeglasses, the 3D display being configured to display video from a surgical robotics camera wherein the two micro-lenses layers are arranged over the panel display, and a spacer is disposed between the panel display and a protective layer that is arranged over the two micro-lenses layers; and
a processor that is configured to
track a position of the eyes of a user relative to the 3D display, and
adjust a position or an orientation of the 3D display relative to the eyes of the user, to maintain a prescribed distance between the eyes of the user and the 3D display, and to center the eyes of the user relative to the 3D display to support the visualization of the three-dimensional images on the 3D display.

2. The display system of claim 1, further comprising one or more actuators to adjust the position or the orientation of the 3D display in response to a signal from the processor.

3. The display system of claim 2, wherein the one or more actuators are mechanically coupled to the 3D display.

4. The display system of claim 2, wherein the one or more actuators are mechanically coupled to a seat of the user.

5. The display system of claim 1, further comprising a camera to generate an output used by the processor to track the position of the eyes of the user relative to the 3D display.

6. The display system of claim 1, wherein the 3D display includes a second protective layer arranged between the panel display and the two micro-lenses layers.

7. The display system of claim 6, wherein the 3D display includes a second spacer between the protective layer and the panel display.

8. The display system of claim 7, wherein the 3D display includes an adhesive between the protective layer and the two micro-lenses layers.

9. A method, comprising:
displaying video from a surgical robotics camera to an autostereoscopic three-dimensional (3D) display comprising a panel display and a-two micro-lenses layers positioned over the panel display to display a left eye image and a right eye image for visualization of three-dimensional images on the 3D display without use of eyeglasses wherein the two micro-lenses layers are arranged over the panel display, and a spacer is disposed between the panel display and a protective layer that is arranged over the two micro-lenses layers;
tracking a position of the eyes of a user relative to the 3D display; and
adjusting a position or an orientation of the 3D display relative to the eyes of the user, to maintain a prescribed distance between the eyes of the user and the 3D display, and to center the eyes of the user relative to the 3D display to support the visualization of the three-dimensional images on the 3D display.

10. The method of claim 9, wherein adjusting the position or the orientation of the 3D display includes signaling one or more actuators to adjust the position or the orientation of the 3D display.

11. The method of claim 10, wherein the one or more actuators are mechanically coupled to the 3D display.

12. The method of claim 10, wherein the one or more actuators are mechanically coupled to a seat of the user.

13. The method of claim 9, wherein tracking the position of the eyes of the user relative to the 3D display is performed based on an output of a camera.

14. The method of claim 9, wherein the 3D display includes a second protective layer arranged between the panel display and the two micro-lenses layers.

15. The method of claim 14, wherein the 3D display includes a second spacer between the two micro-lenses layers and the panel display.

16. The method of claim 15, wherein the 3D display includes an adhesive between the protective layer and the two micro-lenses layers.

* * * * *